United States Patent
Alberati et al.

(10) Patent No.: US 9,877,963 B2
(45) Date of Patent: Jan. 30, 2018

(54) GLYT1 INHIBITORS FOR USE IN THE TREATMENT OF HEMATOLOGICAL DISORDERS

(71) Applicant: Hoffmann-La Roche Inc., Little Falls, NJ (US)

(72) Inventors: Daniela Alberati, Grenzach-Wyhlen (DE); Annette Koerner, Grenzach-Wyhlen (DE); Emmanuel Pinard, Linsdorf (FR); Michael Winter, Freiburg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/334,722

(22) Filed: Oct. 26, 2016

(65) Prior Publication Data

US 2017/0042888 A1 Feb. 16, 2017

(30) Foreign Application Priority Data

Apr. 30, 2014 (EP) .................... 14166497

(51) Int. Cl.
| | | |
|---|---|---|
| A61K 31/496 | (2006.01) | |
| A61K 31/437 | (2006.01) | |
| A61P 7/00 | (2006.01) | |
| A61P 7/06 | (2006.01) | |

(52) U.S. Cl.
CPC .......... *A61K 31/496* (2013.01); *A61K 31/437* (2013.01)

(58) Field of Classification Search
CPC ............................ A61K 31/496; A61K 31/437
See application file for complete search history.

(56) References Cited

FOREIGN PATENT DOCUMENTS

| JP | 2007-501820 A | 1/2007 |
| JP | 2008-529982 A | 7/2008 |
| WO | 2005/014563 A1 | 2/2005 |
| WO | 2006/082001 A1 | 8/2006 |

OTHER PUBLICATIONS

Definition of prevent, Princeton University "About WordNet." WordNet. Princeton University. 2010. <http://wordnet.princeton.edu>, accessed Sep. 18, 2012.*
Higgs et al. PNAS 2008, 105 (33) 11595-11596.*
Alexander et al. Genetics in Medicine 2009, 11 (5), 307-313.*
Pinard et al. J. Med. Chem. 2010, 53, 4603-4614.*
NIH U.S. National Library of Medicine <https://meshb.nlm.nih.gov/record/ui?ui=D006402>, accessed Jul. 10, 2017.*
Abdulmalik et al. Expert opinion on Therapeutics patents 2005, 15 (11), 1497-1506.*
ISR for PCT/EP2015/059037.
Kiessling Katrina et al., "A comparison in normal individuals and sickle cell patients of reduced glutathione precursors and their transport between plasma and red cells" The Hematology Journal 1: 243-249 ( 2000).
Osheiza Abdulmalik et al., "Sickle cell disease: current therapeutic approaches" Expert Opinion on Therapeutic Patents 15(11):1497-1506 (Nov. 1, 2005).

* cited by examiner

*Primary Examiner* — Irina Neagu
(74) *Attorney, Agent, or Firm* — Brian L. Buckwalter (57) ABSTRACT

The invention is related to compounds, which are GlyT1 inhibitors, for use in the treatment of hematological disorders, in particular for use in the treatment of sickle cell disease and thalassemia, or for the treatment of patients with iron overload syndromes, such as hereditary hemochromatosis.

14 Claims, 3 Drawing Sheets

GLYT1 INHIBITORS FOR USE IN THE TREATMENT OF HEMATOLOGICAL DISORDERS

CROSS REFERENCE TO RELATED APPLICATIONS

This application is a continuation of International Application No. PCT/EP2015/059037 having an international filing date of Apr. 27, 2015 and which claims benefit under 35 U.S.C. § 119 to European Patent Application No. 14166497.9 filed Apr. 30, 2014. The entire contents of both are incorporated herein by reference.

FIELD OF THE INVENTION

The present invention relates to novel methods to treat hemological disorders with GlyT1 inhibitors. The hemological disorders include sickle cell disease, thalassemia and iron overload syndrome, particularly hereditary hemochromatosis. The present invention further relates to pharmaceutical compositions containing GlyT1 and their potential use as medicaments.

BACKGROUND OF THE INVENTION

It is known that glycine transporters inhibitors are suitable for the treatment of neurological and neuropsychiatric disorders. The majority of diseases states implicated are psychoses, schizophrenia (Armer R E and Miller D J, *Exp. Opin. Ther. Patents*, 11 (4): 563-572, 2001), psychotic mood disorders such as severe major depressive disorder, mood disorders associated with psychotic disorders such as acute mania or depression, associated with bipolar disorders and mood disorders, associated with schizophrenia, (Pralong E T et al., *Prog. Neurobiol.*, 67: 173-202, 2002), autistic disorders (Carlsson M L, *J. Neural Trans.*, 105: 525-535, 1998), cognitive disorders such as dementias, including age related dementia and senile dementia of the Alzheimer type, memory disorders in a mammal, including a human, attention deficit disorders and pain (Armer R E and Miller D J, *Exp. Opin. Ther. Patents*, 11 (4): 563-572, 2001). Thus, increasing activation of NMDA receptors via GlyT-1 inhibition may lead to agents that treat psychosis, schizophrenia, dementia and other diseases in which cognitive processes are impaired, such as attention deficit disorders or Alzheimer's disease.

Although sickle cell disease and its clinical manifestations have been recognized within West Africa for several centuries, the first report of sickle cell disease appearing in the medical literature occurred only in 1910 by James B. Herrick.

Worldwide, it is believed that there are in excess of four million sickle cell disease patients today. The majority of them are in Africa, mostly in the Central and Western regions. About 100.000 patients, primary of African or Latin origin, live in the USA, another 100.000 are in Europe. The disease also affects four to five million people in the Middle East, India, South America and the Caribbean.

This hereditary condition is believed to have started in the Western and Central parts of Africa. In those areas, sickle cell trait or carrier status was beneficial because the single gene actually protected a person from malaria. As a result, those with the gene survived the malaria epidemic in the affected regions of Africa. However, people who inherited the affected gene from both parents, had the condition called sickle cell anemia.

Aside from sickle cell anemia, other genetic changes can result in similar conditions and are categorized under sickle cell disease. Sickle cell anemia is the most common type of the sickle cell disease. Other major conditions in the same category include: SC disease (a combination of sickle mutation and hemoglobin C mutation) and Sβ-thalassemia or Sα-thalassemia (a combination of sickle mutation and β-thalassemia mutation or α-thalassemia). In all of these conditions, patients can have severe painful episodes and organ damage.

Sickle cell anemia and the existence of sickle hemoglobin (Hb S) was the first genetic disease to be understood at the molecular level. It is recognized today as a morphological and clinical result of a glycine to valine substitution at the 6 position of the beta globin chain. The major source of morbidity and mortality of patients suffering from sickle cell disease is vascular occlusion caused by sickle cells, which causes repeated episodes of pain in both acute and chronic form and causes also ongoing organ damage with the passage of time.

The deformation and distortion of sickle cell erythrocytes upon complete de-oxygenation is caused by polymerization and intracellular gelation of sickle hemoglobin S. The intracellular gelatin and polymerization of Hb S can occur at any time during erythrocyte's journey through the vasculature. Thus, erythrocytes in patients with sickle cell disease containing no polymerized hemoglobin S may pass through the microcirculation and return to the lungs without sickling, but may sickle in the veins or may sickle in the capillaries. For red cells that sickle within the capillaries, a number of possible consequent events exist, ranging from no effect on transit time, to transmit occlusion of the capillary, to a more permanent blockage that may ultimately result in ischemia or infarction of the surrounding cells, and in the destruction of the red cell. When the blood vessels are blocked, oxygen and nutrients cannot be carried to the area covered by the affected blood vessels and tissue in the area will die and cause severe inflammation and heart attacks. This happens not just once or twice, but closer to several times a year.

Today, there are limited measures for treating sickle cell disease. The use of antibiotics over the last 50 years has done much to prevent deadly infection among children with this disease, leading to major improvements in survival rates in developed countries. The only cure for sickle cell disease is stem cell transplantation; however, this is available to a very limited number of patients due to scarcity of matched donors.

Since the mid 90's, an oral medication called hydroxyurea has been available for prevention of "painful crises". For those who can take this medication on a regular basis, it has improved their quality life immensely. However, it is a medicine that was originally designed for certain types of cancer and has many side effects, including suppression of white blood cells that fight infection, skin ulcers, stomach problems and anemia.

BRIEF DESCRIPTION OF THE INVENTION

The invention is related to compounds, which are GlyT1 inhibitors, for use in the treatment of hematological disorders, in particular for use in the treatment of sickle cell disease and thalassemia, or for the treatment of patients with iron overload syndromes, such as hereditary hemochromatosis.

Another aspect of the In another aspect of the invention relates the use of GlyT1 inhibitors of formula (I) for use in the treatment of hematological disorders.

wherein
R¹ is halogen, lower alkyl substituted by halogen, cyano or S(O)₂-lower alkyl;
R² is lower alkyl, lower alkyl substituted by halogen or is (CH₂)ₒ-cycloalkyl;
R³ is lower alkyl, NH₂ or amino-substituted by one or two lower alkyl;
X C or N;
n is 1 or 2;
o is 0, 1 or 2;
as well as pharmaceutically acceptable acid addition salts thereof.

The compounds of formula I are known and described in WO2005/014563, together with their processes for preparation.

Another aspect of the In another aspect of the invention relates the use of GlyT1 inhibitors of formula (II) for use in the treatment of hematological disorders.

wherein
R¹ is halogen, lower alkyl, lower alkyl substituted by halogen, lower alkoxy, cyano or S(O)₂-lower alkyl;
R² is lower alkyl, lower alkyl substituted by halogen or is (CH₂)ₒ-cycloalkyl;
R³ is lower alkyl, NH₂ or amino-substituted by one or two lower alkyl;
X is C or N;
X¹ is C or N; wherein only one of X and X¹ is N;
n is 1 or 2;
o is 0, 1 or 2;
as well as pharmaceutically acceptable acid addition salts thereof.

The compounds of formula II are known and described in WO2006/082001, together with their processes for preparation.

Another aspect of the invention relates to a pharmaceutical composition comprising GlyT1 inhibitors for use in the treatment of hematological disorders comprising a compound according to the invention and a pharmaceutically acceptable carrier.

DETAILED DESCRIPTION OF THE INVENTION

Now it has been found that the compounds of formula I and II may be used for the treatment of hematological diseases like sickle cell disease and thalassemia or for the treatment of the iron overload syndrome, such as hereditary hemochromatosis.

One aspect of the invention relates to GlyT1 inhibitors of formula I for use in the treatment of diseases as describe above, wherein the GlyT1 inhibitor is selected from a compound of formula wherein
R¹ is halogen, lower alkyl substituted by halogen, cyano or S(O)₂-lower alkyl;
R² is lower alkyl, lower alkyl substituted by halogen or is (CH₂)ₒ-cycloalkyl;
R³ is lower alkyl, NH₂ or amino-substituted by one or two lower alkyl;
X C or N;
n is 1 or 2;
o is 0, 1 or 2;
as well as pharmaceutically acceptable acid addition salts thereof.

The compounds of formula I are known and described in WO2005/014563, together with their processes for preparation. The following specific examples relate to compounds of formula I:

[4-(2-fluoro-4-methanesulfonyl-phenyl)-piperazin-1-yl]-(2-isopropoxy-5-methanesulfonyl-phenyl)-methanone
[5-methanesulfonyl-2-(2,2,2-trifluoro-1-methyl-ethoxy)-phenyl]-[4-(5-trifluoromethyl-pyridin-2-yl)-piperazin-1-yl]-methanone
4-isopropoxy-N-methyl-3-[4-(4-trifluoromethyl-phenyl)-piperazine-1-carbonyl]-benzenesulfonamide or
[4-(3-fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.

One further object of the invention relates to compounds of formula II for use in the treatment of diseases as describe above, wherein the GlyT1 inhibitor is selected from a compound of formula:

wherein
R$^1$ is halogen, lower alkyl, lower alkyl substituted by halogen, lower alkoxy, cyano or S(O)$_2$-lower alkyl;
R$^2$ is lower alkyl, lower alkyl substituted by halogen or is (CH$_2$)$_o$-cycloalkyl;
R$^3$ is lower alkyl, NH$_2$ or amino-substituted by one or two lower alkyl;
X is C or N;
X$^1$ is C or N; wherein only one of X and X$^1$ is N;
n is 1 or 2;
o is 0, 1 or 2;
as well as pharmaceutically acceptable acid addition salts thereof.

The compounds of formula II are known and described in WO2006/082001, together with their processes for preparation. The following specific examples relate to compounds of formula II:
[5-methanesulfonyl-2-((S)-2,2,2-trifluoro-1-methyl-ethoxy)-phenyl]-(3-trifluoromethyl-5,7-dihydro-pyrrolo[3,4-b]pyridin-6-yl)-methanone
[5-methanesulfonyl-2-((S)-2,2,2-trifluoro-1-methyl-ethoxy)-phenyl]-(6-trifluoromethyl-1,3-dihydro-pyrrolo[3,4-c]pyridin-2-yl)-methanone or
[5-methanesulfonyl-2-((S)-2,2,2-trifluoro-1-methyl-ethoxy)-phenyl]-(5-methoxy-6-trifluoromethyl-1,3-dihydro-isoindol-2-yl)-methanone.

Now it has been found that the present compounds of formulas I and II due to a unique mechanism of action and well-defined dose-dependent effects, may reduce the production of heme and hemoglobin and the absorption of iron in the developing erythroblasts and reticulocytes. This effect offers the opportunity to induce production of microcytic hypochromic cells in diseases which would benefit from a reduction in the intracellular Hb concentration, and to reduce erythropoietic iron absorption in diseases characterized by oxidant damage and increased erythroid uptake of iron.

In all animal studies it was observed that the cellular Hb value (MCH) was reduced dose-dependently, to a maximum of about 20% at the highest doses, if treated with a compound of formula I or II. In consequence a regenerative micocroytic erythropoisesis developed into a normochromic or hypochromic stage, leading to reduced systemic Hb level in all species tested (mouse, rat, cynomolgus monkey and human).

Therefore, the present compounds of formulas I and II may be useful in the treatment of hematology disorders, in particular for use in sickle cell disease and thalassemia, or for the treatment of the iron overload syndrome, such as hereditary hemochromatosis.

The object of the present invention is to provide compounds of formulas I and II as described herein, for use in the treatment of sickle cell disease.

One further object of the present invention is to provide compounds of formulas I and II for use in the treatment of thalassemia.

One further object of the present invention is to provide compounds of formulas I and II for use in the treatment of the iron overload syndrome, such as hereditary hemochromatosis.

One further object of the present invention is the use of the specific compound of formula I, which compound is

[4-(3-fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.

One further object of the present invention is the use of the specific compound of formula II, which compound is

[5-methanesulfonyl-2-((S)-2,2,2-trifluoro-1-methyl-ethoxy)-phenyl]-(3-trifluoromethyl-5,7-dihydro-pyrrolo[3,4-b]pyridin-6-yl)-methanone.

One object of the invention relates to a method for the treatment or prevention of hematological disorders, in particular for use in sickle cell disease and thalassemia, or for the treatment of patients with an iron overload syndrome, such as hereditary hemochromatosis, in a subject in need of such treatment, which comprises administering to said subject a therapeutically effective amount of a GlyT1 inhibitor as described herein.

One further object of the invention relates to a pharmaceutical composition comprising a GlyT1 inhibitor as described herein in a pharmaceutically acceptable form for the treatment or prevention of hematological disorders, in particular for use in sickle cell disease and thalassemia, or for the treatment of the iron overload syndrome, such as hereditary hemochromatosis.

A further aspect of the invention relates to the use of a GlyT1 inhibitor as described herein for the preparation of medicaments for the treatment or prevention of hematological disorders, in particular for use in sickle cell disease and thalassemia, or for the treatment of patients with an iron overload syndrome, such as hereditary hemochromatosis.

The following definitions of the general terms used in the present description apply irrespectively of whether the terms in question appear alone or in combination with other groups.

The term "lower alkyl", alone or in combination with other groups, stands for a hydrocarbon radical which may be linear or branched, with single or multiple branching, wherein the alkyl group in general comprises 1 to 6 carbon atoms, for example, methyl, ethyl, propyl, isopropyl, n-butyl, i-butyl, 2-butyl, t-butyl, isopentyl, 2-ethyl-propyl, 1,2-dimethyl-propyl and the like.

The terms "lower alkyl substituted by halogen" or "lower alkyl substituted by hydroxy" refers to $C_{1-6}$-alkyl as defined herein, which is substituted by one or multiple halogen or hydroxy, for example $CF_3$, $CH(CH_3)CF_3$, $CH_2CF_2CF_3$, $CH_2CF_2CHF_2$, $C(CH_3)_2OH$ or $CH(CH_3)$ OH.

The terms "halogen" alone or in combination with other groups, denotes chloro (Cl), iodo (I), fluoro (F) and bromo (Br). The preferred "halogen" is F.

The term "cycloalkyl" denotes a monovalent saturated monocyclic hydrocarbon group of 3 to 6 ring carbon atoms. Examples for monocyclic cycloalkyl are cyclopropyl, cyclobutyl, cyclopentyl or cyclohexyl.

The term "pharmaceutically acceptable salt" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid, sulphuric acid, tartaric acid, trifluoroacetic acid and the like. Particular are formic acid, trifluoroacetic acid and hydrochloric acid. Particular are hydrochloric acid, trifluoroacetic acid and fumaric acid.

The corresponding pharmaceutically acceptable salts with acids can be obtained by standard methods known to the person skilled in the art, e.g. by dissolving the compound of formula I in a suitable solvent such as e.g. dioxane or THF and adding an appropriate amount of the corresponding acid. The products can usually be isolated by filtration or by chromatography. The conversion of a compound of formula (I) or (II) into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation.

EXPERIMENTAL DATA

Figure 2:
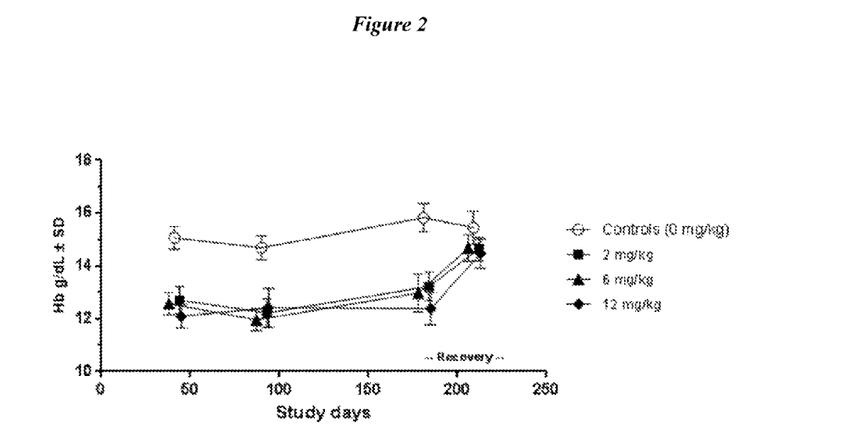
FIG. 2—Effect of [5-methanesulfonyl-2-((S)-2,2,2-trifluoro-1-methyl-ethoxy)phenyl]-(3-trifluoromethyl-5,7-dihydro-pyrrolo[3,4-b]pyridin-6-yl)-methanone on mean group hemoglobin in female rats (26-week study).
Figure 3:
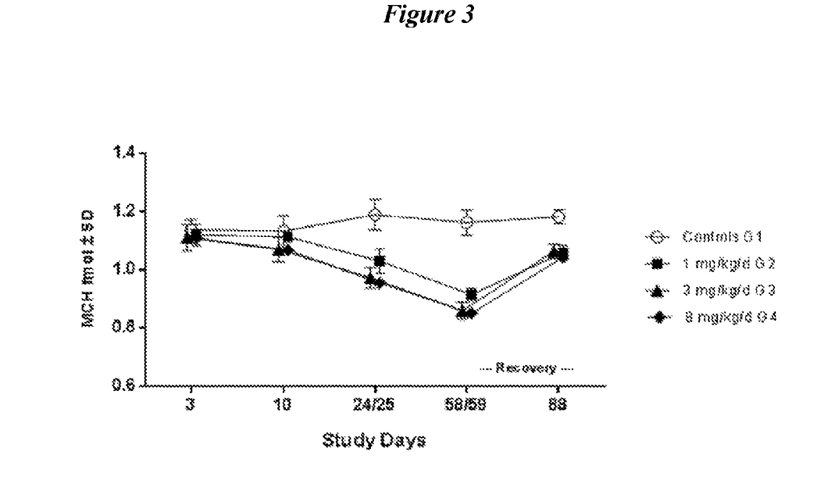
FIG. 3—Effect of 4-(3-fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone on mean group mean corpuscular hemoglobin (MCH) in female rats (8-week study).
Figure 4:
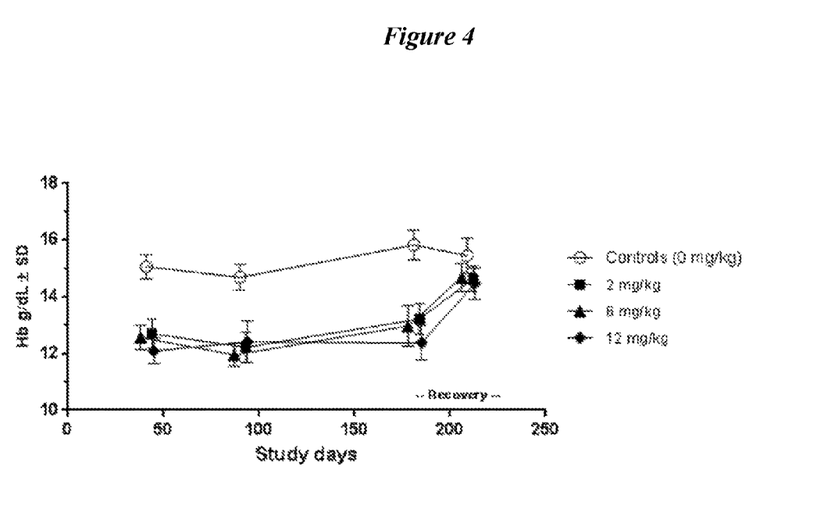
FIG. 4—Effect of [5-methanesulfonyl-2-((S)-2,2,2-trifluoro-1-methyl-ethoxy)phenyl](3-trifluoromethyl-5,7-dihydro-pyrrolo[3,4-b]pyridin-6-yl)-methanone on mean group MCH in female rats (26-week study).

Exposure to [4-(3-fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone and [5-Methanesulfonyl-2-((S)-2,2,2-trifluoro-1-methyl-ethoxy)-phenyl]-(3-trifluoromethyl-5,7-dihydro-pyrrolo[3,4-b]pyridin-6-yl)-methanone induced in rats at all dose levels a microcytic, hypochromic erythropoiesis, characterized by reduction of total hemoglobin concentration (FIGS. 1 and 2) as well as by a reduction of intracellular hemoglobin, MCH (FIGS. 3 and 4). The overall maximal decrease in total hemoglobin concentration did not exceed 20% and the effect was reversible upon treatment cessation.

Figure 1:
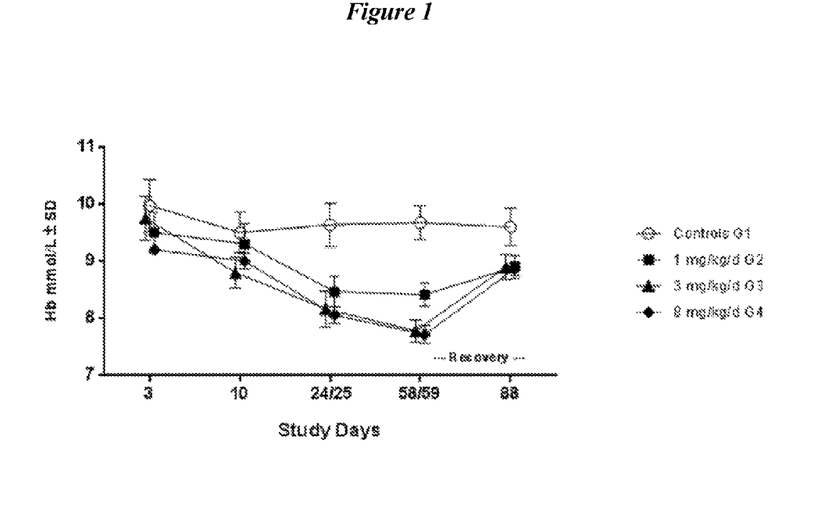
FIG. 1—Effect of 4-(3-fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone on mean group hemoglobin in female rats (8-week study).

Figure 1 Effect of 4-(3-fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone on Mean Group Hemoglobin in Female Rats (8-Week Study)

4-(3-Fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone was administered daily for 8-weeks by dietary admix to female Wistar rats to achieve doses of 1, 3, and 8 mg/kg/day, followed by a 4-week recovery period off treatment. The control group received standard diet only during the whole study period. At various time points during the study hematological parameters including Hb were investigated in peripheral blood using a SYSMEX XT analyser. Data represent group mean values and error bars indicate standard deviation (SD).

Figure 2 Effect of [5-Methanesulfonyl-2-((S)-2,2,2-trifluoro-1-methyl-ethoxy) phenyl]-(3-trifluoromethyl-5,7-dihydro-pyrrolo[3,4-b]pyridin-6-yl)-methanone on Mean Group Hemoglobin in Female Rats (26-Week Study)

[5-Methanesulfonyl-2-((S)-2,2,2-trifluoro-1-methyl-ethoxy) phenyl]-(3-trifluoromethyl-5,7-dihydro-pyrrolo[3,4-b]pyridin-6-yl)-methanone was administered daily for 26-weeks by oral gavage to 20 females Wistar rats per group at doses of 2, 6 and 12 mg/kg/day, followed by a 4-week recovery period off treatment for which 6 additional females where allocated per dose group. The control group was treated with a vehicle control during the dosing period. At various time points during the study hematological parameters including Hb were investigated in peripheral blood using the Bayer, ADVIA 120 hematology analyser. Data represent group mean values and error bars indicate the standard deviation (SD).

Figure 3 Effect of 4-(3-fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone on Mean Group MCH in Female Rats (8-Week Study)

4-(3-fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone was administered daily for 8-weeks by dietary admix to female Wistar rats to achieve doses of 1, 3, and 8 mg/kg/day followed by a 4-week recovery period off treatment. The control group received standard diet during the whole study period. At various time points during the study hematological parameters including MCH were investigated in peripheral blood using a SYSMEX XT analyser. Data represent group mean values and error bars indicate the standard deviation (SD).

Figure 4 Effect of [5-Methanesulfonyl-2-((S)-2,2,2-trifluoro-1-methyl-ethoxy)phenyl](3-trifluoromethyl-5,7-dihydro-pyrrolo[3,4-b]pyridin-6-yl)-methanone on Mean Group MCH in Female Rats (26-Week Study)

[5-Methanesulfonyl-2-((S)-2,2,2-trifluoro-1-methyl-ethoxy)phenyl](3-trifluoromethyl-5,7-dihydro-pyrrolo[3,4-b]pyridin-6-yl)-methanone was administered daily for 26-weeks by oral gavage to 20 females Wistar rats per group at doses of 2, 6 and 12 mg/kg/day, followed by a 4-week recovery period off treatment for which 6 additional females where allocated per dose group. The control group was treated with a vehicle control during the dosing period. At various time points during the study hematological parameters including Hb were investigated in peripheral blood using the Bayer, ADVIA 120 haematology analyser. Data represent group mean values and error bars indicate the standard deviation (SD).

In addition 4-(3-fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone induced a dose-dependent decrease of soluble transferrin receptor (sTfrR), a truncated form of the protein expressed by bone marrow erythroblasts in peripheral blood sample of cynomolgus monkeys treated with 4-(3-fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone (FIG. 5), indicative of a diminished iron uptake in these cells.

Figure 5:
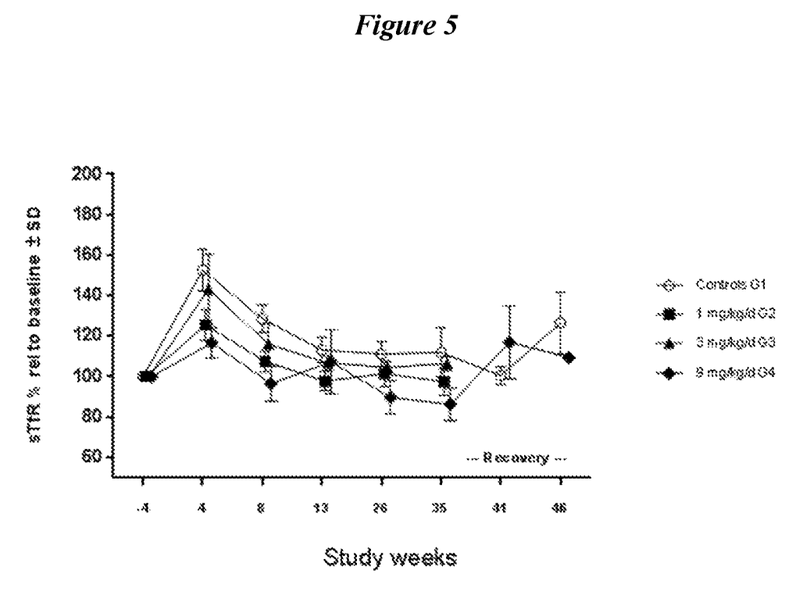
FIG. 5—Effect of 4-(3-fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone on sTrfR (soluble transferrin receptor) in female cynomolgus monkeys

Figure 5 Effect of 4-(3-fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone on sTrfR in Female Cynomolgus Monkeys 4-(3-fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone was administered by capsule via oral gavage to 4 male and 4 female cynomolgus monkeys per group at dose levels of control vehicle, 1, 3 and 9 mg/kg/day for 36 weeks. An additional 2 animals per sex from the control and high-dose group were maintained for an additional 13-week recovery period for assessment of reversibility of any findings. Measurement of sTfR was performed on various occasions during the study in peripheral blood samples. Measurements were done using a SIS-CAPA Assay Technologies Inc. developed assay, designed to identify the soluble fragment of the human transferrin receptor (sTfR) in serum, plasma and blood using the SISCAPA® workflow in combination with mass spectrometry. The human assay was adapted and validated for cynomolgus sTf measurements. Data shown represent group mean values, error bars indicate the standard deviation.

Pharmaceutical Composition

A compound of formula I or II as well as their pharmaceutically acceptable salts can be used as medicaments, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

A compound of formulae I or II and their pharmaceutically acceptable salts can be processed with pharmaceutically inert, inorganic or organic excipients for the production of tablets, coated tablets, dragées and hard gelatin capsules. Lactose, corn starch or derivatives thereof, talc, stearic acid or its salts etc. can be used as such excipients e.g. for tablets, dragées and hard gelatin capsules. Suitable excipients for soft gelatin capsules are e.g. vegetable oils, waxes, fats, semisolid and liquid polyols etc.

Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, in the case of oral administration a daily dosage of about 10 to 1000 mg per person of a compound of formulae should be appropriate, although the above upper limit can also be exceeded when necessary.

Examples of compositions according to the invention are, but are not limited to:

Example A

Tablets of the following composition are manufactured in the usual manner:

| ingredient | mg/tablet | | | |
|---|---|---|---|---|
| | 5 | 25 | 100 | 500 |
| Compound of formula I or II | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

| ingredient | mg/capsule | | | |
|---|---|---|---|---|
| | 5 | 25 | 100 | 500 |
| Compound of formula I or II | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

A compound of formula I or II, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the following composition are manufactured:

| ingredient | mg/capsule |
|---|---|
| Compound of formula I or II | 5 |
| Yellow wax | 8 |
| Hydrogenated Soya bean oil | 8 |
| Partially hydrogenated plant oils | 34 |
| Soya bean oil | 110 |
| Total | 165 |

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

A compound of formula I or II is dissolved in a warm melting of the other ingredients and the mixture is filled into soft gelatin capsules of appropriate size. The filled soft gelatin capsules are treated according to the usual procedures.

Example C

Suppositories of the following composition are manufactured:

| Ingredient | mg/supp. |
|---|---|
| Compound of formula I or II | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

| Ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

A compound of formula I or II is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

| ingredient | mg/sachet |
|---|---|
| Compound of formula I or II | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

A compound of formula I or II is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

We claim:

1. A method of treating a hematological disorder characterized by elevated cellular hemoglobulin (Hb) levels comprising administering to a patient in need thereof a therapeutically effective amount of a GlyT1 inhibitor of formula I:

wherein $R^1$ is independently in each occurrence halogen, lower haloalkyl, cyano or $S(O)_2$-lower alkyl;

$R^2$ is lower alkyl, lower alkyl substituted by halogen or is $(CH_2)_0$-cycloalkyl;

R³ is lower alkyl, NH₂ or amino-substituted by one or two lower alkyl;
X C or N;
n is 1 or 2;
o is 0, 1 or 2; or
an enantiomer thereof, or a pharmaceutically acceptable acid addition salt thereof.

2. The method of claim 1 wherein the disorder is sickle cell disease.

3. The method of claim 1 wherein the disorder is thalassemia.

4. The method of claim 1 wherein the disorder is iron overload syndrome.

5. The method of claim 4 wherein the iron overload syndrome is hereditary hemochromatosis.

6. The method of claim 1 wherein the GlyT1 inhibitor is selected from the group consisting of:
[4-(2-fluoro-4-methanesulfonyl-phenyl)-piperazin-1-yl]-(2-isopropoxy-5-methanesulfonyl-phenyl)-methanone;
[5-methanesulfonyl-2-(2,2,2-trifluoro-1-methyl-ethoxy)-phenyl]-[4-(5-trifluoromethyl-pyridin-2-yl)-piperazin-1-yl]-methanone;
4-isopropoxy-N-methyl-3-[4-(4-trifluoromethyl-phenyl)-piperazine-1-carbonyl]-benzenesulfonamide; and,
[4-(3-fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.

7. The method of claim 6 wherein the GlyT1 inhibitor is a compound of formula Ia (Ia)

[4-(3-fluoro-5-trifluoromethyl-pyridin-2-yl)-piperazin-1-yl]-[5-methanesulfonyl-2-((S)-2,2,2-trifluoro-1-methyl-ethoxy)-phenyl]-methanone.

8. A method of treating a hematological disorder characterized by elevated cellular hemoglobulin (Hb) levels comprising administering to a patient in need thereof a therapeutically effective amount of a GlyT1 inhibitor of formula II:

II wherein
R¹ is independently in each occurrence halogen, lower alkly, lower haloalkly, alkoxy, cyano or S(O)₂-lower alkyl;
R² is lower alkyl, lower alkyl substituted by halogen or is (CH₂)ₒ-cycloalkyl;
R³ is lower alkyl, NH₂ or amino-substituted by one or two lower alkyl;
X and X¹ are N or C, provided both X and X¹ are not N;
n is 1 or 2;
o is 0, 1 or 2;
or an enantiomer thereof, or a pharmaceutically acceptable acid addition salt thereof.

9. The method of claim 8 wherein the GlyT1 inhibitor is selected from the group consisting of:
[5-methanesulfonyl-2-((S)-2,2,2-trifluoro-1-methyl-ethoxy)-phenyl]-(3-trifluoromethyl-5,7-dihydro-pyrrolo[3,4-b]pyridin-6-yl)-methanone;
[5-methanesulfonyl-2-((S)-2,2,2-trifluoro-1-methyl-ethoxy)-phenyl]-(6-trifluoromethyl-1,3-dihydro-pyrrolo[3,4-c]pyridin-2-yl)-methanone; and,
[5-methanesulfonyl-2-((S)-2,2,2-trifluoro-1-methyl-ethoxy)-phenyl]-(5-methoxy-6-trifluoromethyl-1,3-dihydro-isoindol-2-yl)-methanone.

10. The method of claim 9 wherein the GlyT1 inhibitor is a compound of formula IIa (IIa)

[5-methanesulfonyl-2-((S)-2,2,2-trifluoro-1-methyl-ethoxy)-phenyl]-(3-trifluoromethyl-5,7-dihydro-pyrrolo[3,4-b]pyridin-6-yl)-methanone.

11. The method of claim 8 wherein the disorder is sickle cell disease.

12. The method of claim 8 wherein the disorder is thalassemia.

13. The method of claim 8 wherein the disorder is iron overload syndrome.

14. The method of claim 13 wherein the iron overload syndrome is hereditary hemochromatosis.

* * * * *